(12) United States Patent
Li et al.

(10) Patent No.: US 8,735,143 B2
(45) Date of Patent: May 27, 2014

(54) HEPATIC LOBULE-LIKE BIOREACTOR

(75) Inventors: Lanjuan Li, Hangzhou (CN); Chengbo Yu, Hangzhou (CN); Yiming Zhang, Hangzhou (CN); Xiaoping Pan, Hangzhou (CN); Weibo Du, Hangzhou (CN); Hongcui Cao, Hangzhou (CN); Guoliang Lv, Hangzhou (CN); Jianrong Huang, Hangzhou (CN)

(73) Assignee: Zhejiang University, Hangzhou, Zhejiang (CN)

( * ) Notice: Subject to any disclaimer, the term of this patent is extended or adjusted under 35 U.S.C. 154(b) by 0 days.

(21) Appl. No.: 14/005,563

(22) PCT Filed: Mar. 21, 2011

(86) PCT No.: PCT/CN2011/071985
§ 371 (c)(1),
(2), (4) Date: Dec. 6, 2013

(87) PCT Pub. No.: WO2012/122719
PCT Pub. Date: Sep. 20, 2012

(65) Prior Publication Data
US 2014/0087454 A1    Mar. 27, 2014

(30) Foreign Application Priority Data
Mar. 17, 2011 (CN) .......................... 2011 1 0064200

(51) Int. Cl.
*C12M 3/00* (2006.01)
*C12N 5/00* (2006.01)
*A61M 1/14* (2006.01)

(52) U.S. Cl.
CPC .............. *C12N 5/0062* (2013.01); *C12M 3/00* (2013.01); *A61M 1/14* (2013.01)
USPC .................. 435/289.1; 435/370; 435/400

(58) Field of Classification Search
CPC ......... C12N 5/0062; A61M 1/14; C12M 3/00
USPC ...................................... 435/289.1, 370, 400
See application file for complete search history.

(56) References Cited

U.S. PATENT DOCUMENTS 7,393,687 B2 * 7/2008 Geltser ........................ 435/402
8,591,597 B2 * 11/2013 Hoganson et al. ......... 623/23.64

FOREIGN PATENT DOCUMENTS

CN 101129277 A 2/2008
CN 101549181 A 10/2009

OTHER PUBLICATIONS

Li, Jinrong, Advances in biological artificial liver. Foreign Medical Biomedical Engineering Fascicle. 2003, vol. 26, No. 2, pp. 81-84.

(Continued)

*Primary Examiner* — Michael Marcheschi
*Assistant Examiner* — Jonathan Hurst
(74) *Attorney, Agent, or Firm* — Han IP Corporation

(57) ABSTRACT

The present invention provides a hepatic lobule-like bioreactor. The bioreactor includes a nanofiber scaffold enclosed within a housing. An intrahepatic fibrous vascular network, a bile capillary network, upper hepatic bile ducts, lower hepatic bile ducts, a common bile duct connecting the upper and the lower hepatic bile ducts, and collagen fibrous microchannels for hepatocytes surrounded by the bile capillary network are distributed throughout the nanofiber scaffold. Bile capillaries in the bile capillary network are provided with two or more inlet ports for biliary epithelial cells. The collagen fibrous microchannels for hepatocytes are provided with two or more inlet ports for hepatocytes. The intrahepatic vascular network is provided with a liquid inlet port and a liquid outlet port. These ports extend through the housing.

11 Claims, 4 Drawing Sheets

(56) References Cited

OTHER PUBLICATIONS

Marcus, K.H. et al., Morphogenesis of Primary Human Biliary Epithelial Cells: Induction in High-Density Culture or by Coculture With Autologous Human Hepatocytes. Hepatology. Mar. 2001, vol. 33, No. 3, pp. 519-529.

Gerlach, Jorge C. et al., Bioartificial liver systems: why, what, whither?. Regen. Med. 2008, vol. 3, No. 4, pp. 575-595.

Gerlach, Jorge C. et al., Improved Hepatocyte In Vitro Maintenance in a Culture Model With Woven Multicompartment Capillary Systems: Electron Microscopy Studies. Hepatology. Aug. 1995, vol. 22, No. 2, pp. 546-552.

\* cited by examiner

HEPATIC LOBULE-LIKE BIOREACTOR

CROSS-REFERENCE TO RELATED APPLICATION

This application is the national phase application of International application number PCT/CN2011/071985, filed Mar. 21, 2011, which claims the priority benefit of China Patent Application No. 201110064200.X, filed Mar. 17, 2011. The above-identified applications are hereby incorporated by reference in their entirety.

TECHNICAL FIELD

The present invention relates generally to the field of biomedical devices. Specifically, the present invention relates to bionic liver tissue engineering involving mimicking structural units of a natural liver, and in particular, relates to a hepatic lobule-like bioreactor, a key component for biological- or hybrid-bioartificial livers.

BACKGROUND

Liver is one of the body's most important organs. It has a complex structure and performs a variety of physiological functions. Acute or chronic liver disease, especially liver failure, has a severe impact on human health. Liver transplantation is a unique and effective approach to treat patients with end-stage liver disease or liver failure. However, its application is greatly limited by the scarcity of donors, the graft failure and the need for long-term use of immunosuppressive agents. Therefore, there remains a need for an alternative approach for treating serious liver diseases. Liver tissue engineering holds promise for the treatment of serious liver diseases.

Tissue engineering has emerged as a new cross-disciplinary field since late 1980s. In recent years, with the development of life science and materials science and engineering, breakthroughs have been achieved in in vitro reconstruction of a variety of tissues and organs, and some of tissue engineered products such as cartilage and skin have now been commercialized. Liver tissue represents an important research direction in tissue engineering. The ultimate goal is to construct a transplantable liver tissue or organ to treat patients with impaired liver function. Liver functions as a plant of the body where chemical synthesis, detoxification, biotransformation, and nutrition processing occur; it is also a place where the complex body supplies adjustment takes place. The tissue structure and physiological functions of the liver are complicated. The liver consists of a myriad of functional units called lobules. The lobule is composed of hepatocytes, bile capillaries, and sinusoids. Through these basic functional units, the liver performs a variety of functions including metabolism, nutrition and excretion of bile. How to construct a fully functional or transplantable tissue engineered liver in vitro remains a major challenge in the liver tissue engineering.

Bioreactor is a key component of a bioartificial liver, at which the material exchange between exogenous hepatocytes and patient's blood or plasma takes place. However, to date, progress in the development of bioreactor has been slow. Materials currently used in bioreactors as well as design configuration and efficacy of bioreactors are far below the desired level. Accordingly, how to design a structure so that bioreactors can more closely mimic the tissue structure of a normal liver, thus providing a living and metabolic environment similar to an in vivo environment for the cultivation of hepatocytes, becomes the most difficult part of future research. As to several types of bioreactors being developed such as flat plate bioreactors, hollow fiber bioreactors, microcapsule suspension bioreactors, and scaffold perfusion bioreactors, configurations of these bioreactors are quite different from the structure of the human liver. These bioreactors do not contain a bile excretion system and suffer low material exchange efficiencies. Therefore, there remains a need to develop new materials as well as an improved bioreactor design, so that the fluid mechanics and geometry of the bioreactor more closely mimic the physiological states. There are no bioreactors in the art having a hepatic lobule-like structure.

SUMMARY

The objective of the present invention is to provide a bioreactor having a hepatic lobule-like structure. The structure of the bioreactor mimics the hepatic structure so as to improve the efficacy of the bioreactor.

To achieve the above objective, the present invention adopts the following technical solutions: the hepatic lobule-like bioreactor includes a closed-housing, and within which a nanofiber scaffold is enclosed. An intrahepatic fibrous vascular network, a bile capillary network, upper hepatic bile ducts, lower hepatic bile ducts, a common bile duct, and collagen fibrous microchannels for hepatocytes are distributed throughout the nanofiber scaffold. The collagen fibrous microchannels for hepatocytes are surrounded by the bile capillary network. The upper hepatic bile ducts are connected to the lower hepatic bile ducts through the common bile duct. The bile capillaries in the bile capillary network are provided with two or more inlet ports for biliary epithelial cells. The collagen fibrous microchannels for hepatocytes are provided with two or more inlet ports for hepatocytes. The intrahepatic fibrous vascular network is provided with a liquid inlet port and a liquid outlet port. The inlet ports for biliary epithelial cells, the inlet ports for hepatocytes, the liquid inlet port, the liquid outlet port, and an outlet port at a lower end of the common bile duct extend through the housing.

In one embodiment, the liquid inlet port of the present invention may be connected to a membrane oxygenator, and the liquid outlet port may be connected to an immune absorber that absorbs immune macromolecules.

In one embodiment, the housing of the present invention may be made of polypropylene or polyethylene.

In one embodiment, the intrahepatic fibrous vascular network of the present invention may be made of polyurethane or expanded polytetrafluoroethylene.

In one embodiment, fibrous veins in the intrahepatic fibrous vascular network of the present invention have a diameter of 50 μm to 6 mm, and a porosity of 85% to 95%.

In one embodiment, the collagen fibrous microchannels for hepatocytes of the present invention may be hollow fibers made of a material selected from the group consisting of polypropylene, polysulfone, polyethersulfone, polyether esters, polyethylene, poly(vinylidene fluoride), and polyetheretherketone.

In one embodiment, the collagen fibrous microchannels for hepatocytes of the present invention may have a diameter of 600 μm to 1 mm.

In one embodiment, the bile capillary network of the present invention may be made of a material selected from the group consisting of polypropylene, polysulfone, polyethersulfone, polyether esters, polyethylene, poly(vinylidene fluoride), and polyetheretherketone.

In one embodiment, the nanofiber scaffold of the present invention may be made of a material selected from the group consisting of polycaprolactone, sodium alginate, chitosan-poly(lactic-co-glycolic acid), poly(L-lactic acid), chitosan-collagen, polyglycolic acid, and a combination thereof.

In one embodiment, the nanofiber scaffold of the present invention may have a diameter of 20 nm to 500 nm and a porosity greater than 80%.

In the present invention, the bioreactor made from biological materials is used in a bioartificial liver. Through rational design to optimize the internal structure of the bioreactor, the clinical efficacy of the bioartificial liver is greatly improved. To improve the performance of the bioreactor in the bioartificial liver, biocompatible materials are adopted in the present invention to construct the bioreactor mimicking the intrahepatic vascular network, through which blood (plasma) or nutrient fluid is carried in or out of the reactor, thus providing nutrition to hepatocytes and facilitating material exchange in the reactor. In addition, by preparing intrahepatic bile capillary network using biomaterials, biliary endothelial cells are seeded in the bile capillaries, thus facilitating the excretion of bilirubin secreted by the hepatocytes to the bile capillaries via biliary endothelial cells. Eventually, the bilirubin is excreted out of the body via the common bile duct. As a result, the bilirubin level in the blood of animal or human with liver failure could be significantly reduced. To construct the bioreactor with a hepatic lobule plate-like structure, the hepatocytes are seeded and cultivated in the fibrous microchannels to form cord-like hepatic plates. These cork-like hepatic plates surround the bile capillaries and perform functions such as detoxification, metabolism, and synthesis as well as material exchange of harmful substances such as bilirubin via the bile capillaries or intrahepatic veins. The current design integrates intrahepatic veins, intrahepatic bile capillaries and hepatic plates in the bioreactor, thus allowing more closely mimic the hepatic lobule structure.

Compared with prior art technologies, the bioreactor of the present invention possesses a number of advantages.

First, the bioreactor of the present invention mimics the structure of the hepatic lobule more closely. The bioreactor includes a lobular vascular network for supplying blood or nutrition to hepatocytes, a hepatic plate structure for metabolism, and an intrahepatic bile duct system for excretion of bile. From the physiological structure point of view, the bioreactor of the present invention offers outstanding advantages over those in the art. Unlike the bioreactor of the present invention, all currently available bioreactors such as flat plate bioreactors, hollow fiber bioreactors, bracket perfusion bioreactors, and microcapsule suspension bioreactors do not truly contain a vascular network, and more importantly they do not contain the most critical component, a biliary excretion system, which are the novel features of the present invention.

Second, in the bioreactor of the present invention, the microchannels of hepatic plates and intrahepatic bile duct network are made by safe and non-toxic materials with good biocompatibility or by modified biomaterials that are suitable for the growth of hepatocytes or biliary epithelial cells. Hepatocytes cultivated in the bioreactor form cord-like hepatic plates. After modifying intrahepatic bile ducts with collagen, co-cultivation of the hepatocytes and biliary epithelial cells forms functional biliary endothelial cells in the intrahepatic bile ducts.

Third, the bioreactor of the present invention includes a special nanofiber scaffold. From in vitro experimental results, the nanofiber scaffold exhibits an excellent mass transfer property, which is very beneficial to the transfer of metabolites. The nanofiber scaffold of the present invention is equivalent to the collagen scaffold distributed throughout the liver.

Fourth, the structure of the hepatic lobule-like bioreactor used for bioartificial livers in the present invention mimics the structure of the human liver more closely. This new concept opens up a new avenue in the bioartificial liver development. The bioreactor of the present invention possesses more comprehensive functions and a more rational design. The bioreactor of the present invention has following novel features: incorporating a biliary excretion system in the bioreactor which has never been demonstrated before; and using a nanofiber scaffold to increase mass transfer performance. The bioreactor of the present invention will generate a huge impact on bioartificial livers and future development of bioreactors.

DETAILED DESCRIPTION OF THE PREFERRED EMBODIMENTS

Figure 1:
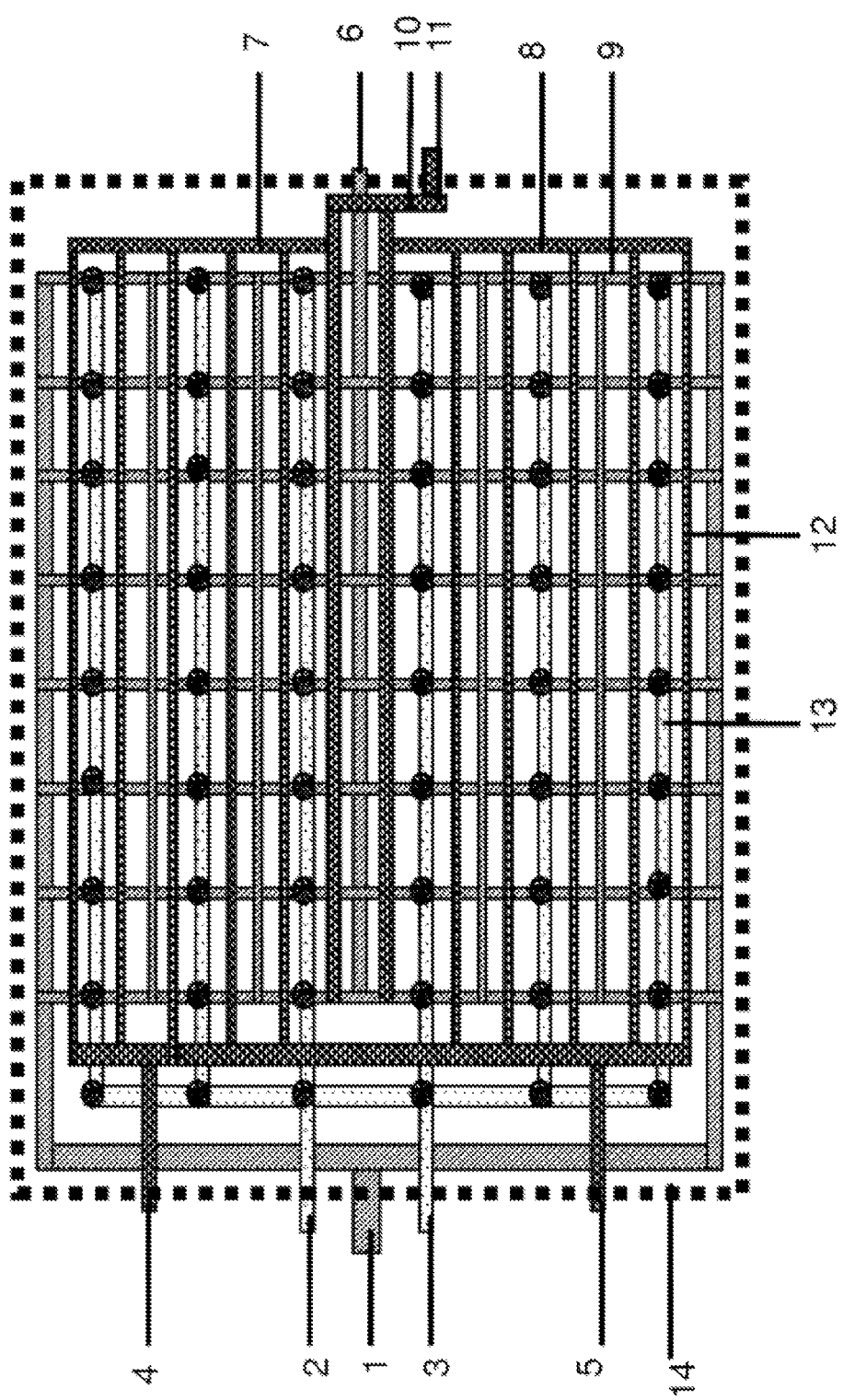
FIG. 1 is a schematic view of a hepatic lobule-like bioreactor of the present invention for bioartificial liver application.
Figure 2:
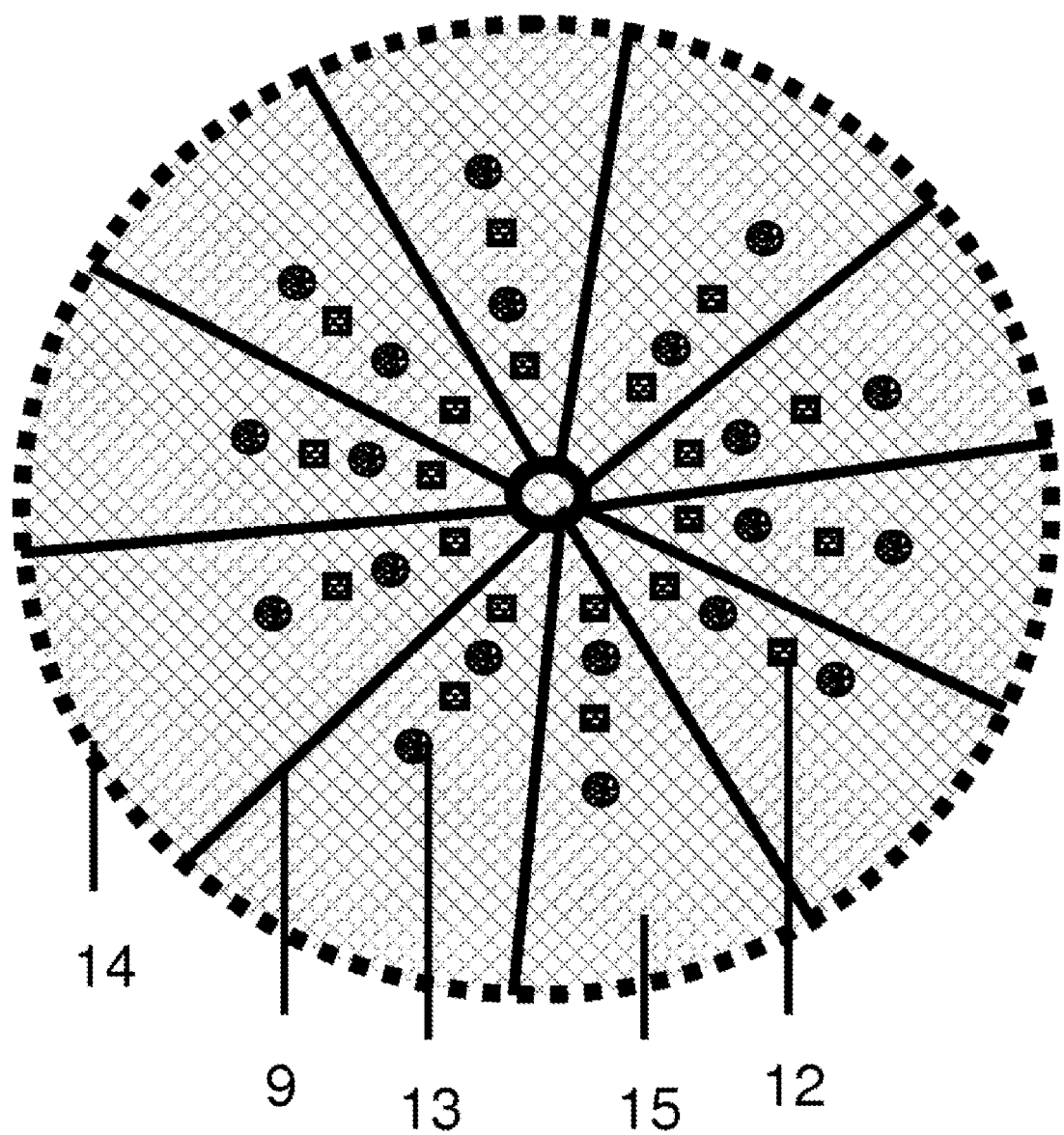
FIG. 2 is a schematic minimized sagittal plane view of the bioreactor of FIG. 1.
Figure 3:
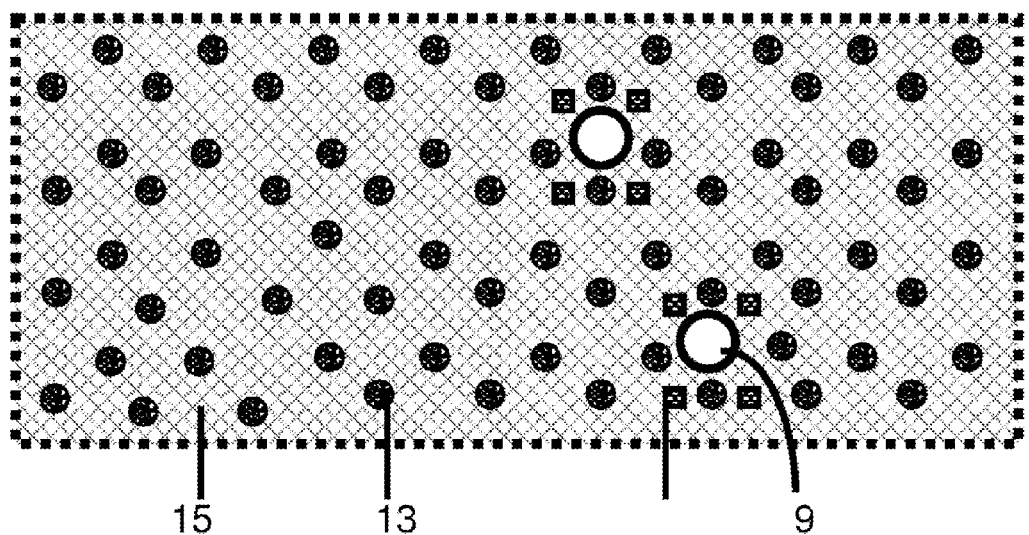
FIG. 3 is a schematic minimized coronal plane view of the bioreactor of FIG. 1.
Figure 4:
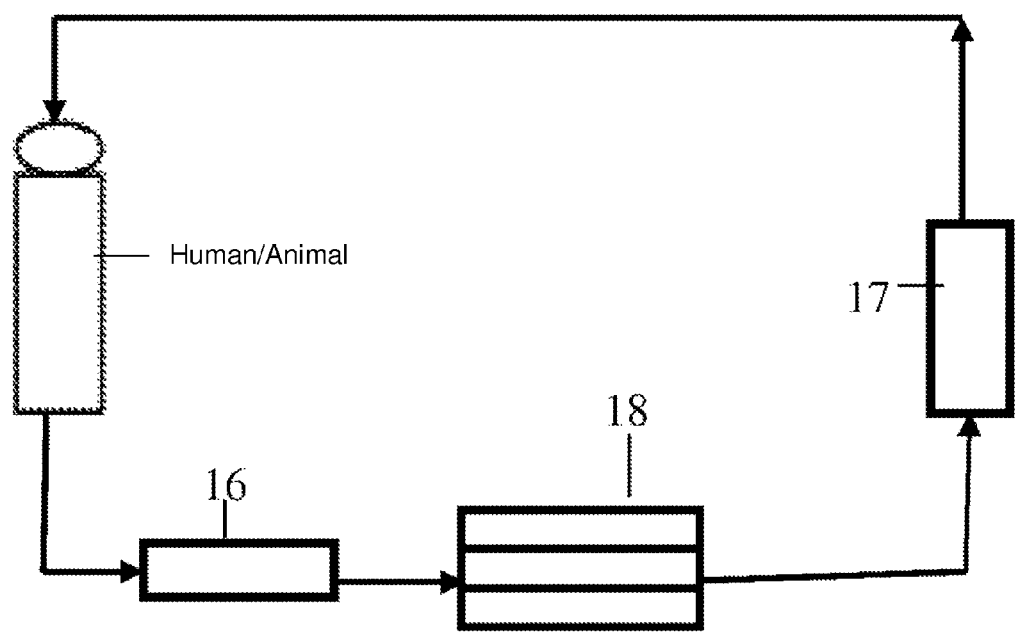
FIG. 4 is a schematic diagram illustrating the bioreactor of the present invention in working condition.

Referring to FIGS. 1 to 3, a hepatic lobule-like bioreactor includes a closed-housing 14, with a nanofiber scaffold 15 enclosed in the housing 14. An intrahepatic fibrous vascular network 9, a bile capillary network 12, upper hepatic bile ducts 7, lower hepatic bile ducts 8, a common bile duct 10, and collagen fibrous microchannels for hepatocytes 13 are distributed throughout the nanofiber scaffold 15, and the collagen fibrous microchannels for hepatocytes 13 are surrounded by the bile capillary network 12. Among them, the upper hepatic bile ducts 7 are connected to the lower hepatic bile ducts 8 via the common bile duct 10. Bile capillaries in the bile capillary network 12 are provided with two or more inlet ports for biliary epithelial cells. The collagen fibrous microchannels 13 for hepatocytes are provided with two inlet ports 2, 3 for hepatocytes. In the present invention, the bioreactor may include three or more inlet ports for biliary epithelial cells and three or more inlet ports for hepatocytes. The intrahepatic fibrous vascular network 9 is provided with a liquid inlet port 1 and a liquid outlet port 6. The inlet ports for biliary epithelial cells, the inlet ports for hepatocytes, the liquid inlet port 1, the liquid outlet port 6, and an outlet port at the lower end of the common bile duct 10 all extend through the housing 14.

For further improvements, the liquid inlet port 1 is connected to a membrane oxygenator 16, and the liquid outlet port 6 is connected to an immune absorber 17 for absorbing immune macromolecules. Examples of preferred housing 14 materials include polypropylene and polyethylene. Examples of materials used to make the intrahepatic fibrous vascular network 9 include polyurethane and expanded polytetrafluoroethylene. The fibrous veins in the intrahepatic fibrous vascular network have a diameter of 50 μm to 6 mm, and a porosity of 85% to 95%. Examples of materials used to make the collagen fibrous microchannels for hepatocytes 13 include hollow fibers of polypropylene, polysulfone, polyethersulfone, polyether esters, polyethylene, poly(vinylidene fluoride), and polyetheretherketone. The collagen fibrous microchannels for hepatocytes 4 have a diameter of 600 μm to 1 mm. Examples of materials used to make the bile capillary network 12 include polypropylene, polysulfone, polyethersulfone, polyether esters, polyethylene, poly(vinylidene fluoride), and polyetheretherketone. Examples of materials used to make the nanofiber scaffold 15 include one or more of polycaprolactone, sodium alginate, chitosan-poly(lactic-co-glycolic acid), poly(L-lactic acid), chitosan-collagen, polyglycolic acid, and a combination thereof. The nanofiber scaffold 15 has a diameter of 20 nm to 500 nm and a porosity greater than 80%.

In the present invention, the housing 14 of the hepatic lobule-like bioreactor may be encapsulated by modified polypropylene or polyethylene. The inlet ports for biliary epithelial cells 4, 5, the inlet ports for hepatocytes 2, 3, the liquid inlet port 1, the liquid outlet port 6, and the outlet port at the lower end of the common bile duct 10 extend through the housing 14. As shown in FIG. 1, the inlet ports and outlet ports are disposed at opposite sides of the housing 14, respectively. These ports are encapsulated by medical grade adhesives. The lobular functional units, including intrahepatic veins, microchannels for hepatocytes, and intrahepatic bile ducts are disposed within the bioreactor. Typically, the hepatic lobule-like bioreactor of the present invention has a length of 15 cm to 25 cm, a diameter of about 6 cm to 8 cm, and a volume of 200 ml to 600 ml. The dimension of the bioreactor may be enlarged or reduced according to needs.

Referring to FIGS. 1 to 4, the bioreactor 18 of the present invention that is in working condition is illustrated below. After entering the bioreactor via the liquid inlet port 1, a culture medium and blood or plasma are circulated in the intrahepatic veins. Inlet ports for hepatocytes are numerated as 2 and 3. After entering the bioreactor via the inlet ports 4 and 5, the biliary epithelial cells are distributed in the bile capillary network, at which they are cultivated for 1-10 days to form a bile duct-like structure. The liquid outlet port 6 is an output channel through which the culture medium and blood or plasma that are converged via the intrahepatic vascular network flow out of the bioreactor after the metabolism and material exchange. The intrahepatic bile capillaries secrets bile into the upper hepatic bile ducts 7 and the lower hepatic bile ducts 8. The intrahepatic fibrous vascular network 9 is the place where material exchange occurs when liquids flow through the intrahepatic capillary vascular network in the bioreactor. Bile flowed into the upper hepatic bile ducts 7 and bile flowed into the lower hepatic bile ducts 8 are converged at the common bile duct 10, and eventually excreted out of the body via the outlet 11 disposed at the common hepatic duct. Since direct bilirubin is excreted out of the body, the direct bilirubin level in the body is reduced. The bile capillary network 12 is the place where the secretion and excretion of bilirubin from the hepatocytes and intrahepatic biliary epithelial cells occur. The collagen fibrous microchannels for hepatocytes 13 are places where hepatocytes grow into a hepatic plate-like structure. The nanofiber scaffold 15 functions as a support for the structural units of the hepatic lobule. The nanofiber scaffold 15 produced by electrospinning has a nonwoven fabric structure to ensure efficient mass transfer among structural units of the hepatic lobule. The housing 14 acts as the medical grade outer shell for the entire bioreactor. Various ports are distributed on opposite sides of the housing 14 with inlets disposed on the left side and the outlets disposed on the right side. The port connection portions are encapsulated by medical grade adhesives. The oxygenation of the plasma and culture medium by the oxygenator 16 supplies requisite oxygen to hepatocytes in the hepatic lobule-like bioreactor. The immune absorber 17 may absorb immune macromolecules (e.g., IgG, IgM and complementary series) to prevent the immune macromolecules from entering the organ. As a result, the immune response may be suppressed.

Only when the appearance and structure of the bioreactor in the in vitro design mimic the hepatic lobule more closely, the resulting bioreactor may perform functions such as metabolism, detoxification and excretion more like the liver. Through constructing lobule-like structural units, including the intrahepatic vascular network, hepatic plates, intrahepatic bile ducts, and common bile duct, the present invention mimics the structure of hepatic lobule more closely. This novel design concept has never been demonstrated in bioreactors in the art.

The effectiveness of the hepatic lobule-like bioreactor of the present was evaluated using a method as described below: taking a D-galactosamine-induced liver failure model in a large animal, pig, after cultivating hepatocytes and biliary endothelial cells of a primary pig separately in the collagen fibrous microchannels for hepatocytes and bile capillaries for 1-3 days, whole blood of the pig with liver failure was led outside of its body via a circulation system established in vitro. After the separation of plasma from the whole blood, the plasma of the pig with liver failure was metabolized by the hepatic lobule-like bioreactor. Meanwhile, at the downstream of the hepatic lobule-like bioreactor, the immune macromolecules were absorbed by the immune absorber to reduce the risk of rejection. It took 4-6 hours for each treatment. Before each treatment, large animal pig's vitality and appetite were observed and its liver function and blood ammonia level were measured. The results indicated that there is a significant improvement in pig's vitality and appetite after treatment. In addition, after treatment, liver enzymes, jaundice index, and blood ammonia level are all decreased. These results suggest that the bioartificial liver with a hepatic lobule-like bioreactor as the key component has a therapeutic effect on the acute liver failure, and can be used to reduce liver damage.

What is claimed is:

1. A hepatic lobule-like bioreactor, comprising:
a closed-housing;
a nanofiber scaffold enclosed within the housing;
an intrahepatic fibrous vascular network where metabolism and material exchange take place, the intrahepatic fibrous vascular network provided with a liquid inlet port and a liquid outlet port;
a bile capillary network, the bile capillary network provided with two or more inlet ports for biliary epithelial cells through which the biliary epithelial cells are distributed and cultivated in the bile capillary network to form a bile duct-like structure;
first hepatic bile ducts;
second hepatic bile ducts;
a common bile duct connecting the first hepatic bile ducts to the second hepatic bile ducts such that bile secreted by bile capillaries in the bile capillary network is converged at the common bile duct via the first and the second hepatic bile ducts and eventually excreted out of a body, the common bile duct provided with an outlet port at one end; and
collagen fibrous microchannels for hepatocytes surrounded by the bile capillary network, the collagen fibrous microchannels provided with two or more inlet ports for hepatocytes through which hepatocytes are distributed and cultivated in the collagen fibrous microchannels to form a hepatic plate-like structure;
wherein the intrahepatic fibrous vascular network, the bile capillary network, the first hepatic bile ducts, the second hepatic bile ducts, the common bile duct, and the collagen fibrous microchannels for hepatocytes are distributed throughout the nanofiber scaffold, and wherein the inlet ports for biliary epithelial cells, the inlet ports for hepatocytes, the liquid inlet port, the liquid outlet port, and the outlet port at one end of the common bile duct extend through the housing.

2. The hepatic lobule-like bioreactor of claim 1, wherein the liquid inlet port is connected to a membrane oxygenator, and wherein the liquid outlet port is connected to an immune absorber that absorbs immune macromolecules.

3. The hepatic lobule-like bioreactor of claim 1, wherein the housing is made of polypropylene or polyethylene.

4. The hepatic lobule-like bioreactor of claim 1, wherein the intrahepatic fibrous vascular network is made of polyurethane or expanded polytetrafluoroethylene.

5. The hepatic lobule-like bioreactor of claim 1, wherein intrahepatic fibrous veins in the intrahepatic fibrous vascular network have a diameter of 50 μm to 6 mm, and a porosity of 85% to 95%.

6. The hepatic lobule-like bioreactor of claim 1, wherein the collagen fibrous microchannels for hepatocytes are hollow fibers made of a material selected from the group consisting of polypropylene, polysulfone, polyethersulfone, polyether esters, polyethylene, poly(vinylidene fluoride), and polyetheretherketone.

7. The hepatic lobule-like bioreactor of claim 1, wherein the collagen fibrous microchannels for hepatocytes have a diameter of 600 μm to 1 mm.

8. The hepatic lobule-like bioreactor of claim 1, wherein the bile capillary network is made of a material selected from the group consisting of polypropylene, polysulfone, polyethersulfone, polyether esters, polyethylene, poly(vinylidene fluoride), and polyether etherketone.

9. The hepatic lobule-like bioreactor of claim 1, wherein the nanofiber scaffold is made of a material selected from the group consisting of polycaprolactone, sodium alginate, chitosan-poly(lactic-co-glycolic acid), poly(L-lactic acid), chitosan-collagen, polyglycolic acid, and a combination thereof.

10. The hepatic lobule-like bioreactor of claim 1, wherein the nanofiber scaffold has a diameter of 20 nm to 500 nm and a porosity greater than 80%.

11. The hepatic lobule-like bioreactor of claim 1, wherein the inlet ports for biliary epithelial cells, the inlet ports for hepatocytes, and the liquid inlet port are disposed at a first side of the housing, and the liquid outlet port and the outlet port at one end of the common bile duct are disposed at a second side of the housing opposite to the first side.

* * * * *